(12) United States Patent
Kang et al.

(10) Patent No.: US 7,968,345 B2
(45) Date of Patent: Jun. 28, 2011

(54) PERMETHYLATION OF OLIGOSACCHARIDES

(75) Inventors: Pilsoo Kang, Bloomington, IN (US); Yehia S. Mechref, Bloomington, IN (US); Milos V. Novotny, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 12/853,759

(22) Filed: Aug. 10, 2010

(65) Prior Publication Data

US 2011/0015386 A1    Jan. 20, 2011

Related U.S. Application Data

(62) Division of application No. 11/817,436, filed as application No. PCT/US2006/007854 on Mar. 3, 2006.

(60) Provisional application No. 60/658,295, filed on Mar. 3, 2005.

(51) Int. Cl.
  *G01N 33/00* (2006.01)
  *C12N 9/26* (2006.01)
(52) U.S. Cl. ......... 436/94; 422/129; 422/68.1; 422/102; 436/43; 436/174; 435/201
(58) Field of Classification Search .................. 435/201; 422/68.1, 102, 129; 436/43, 94, 174
See application file for complete search history.

(56) References Cited

U.S. PATENT DOCUMENTS

| | | |
|---|---|---|
| 5,480,971 A | 1/1996 | Houghten et al. |
| 5,800,979 A | 9/1998 | Kollhouse et al. |
| 6,103,195 A | 8/2000 | Shukla et al. |
| 6,121,489 A | 9/2000 | Dorner et al. |
| 6,444,233 B1 | 9/2002 | Arntzen et al. |
| 7,138,262 B1 * | 11/2006 | Daniel ........................ 435/201 |

* cited by examiner

*Primary Examiner* — Brian J Sines
(74) *Attorney, Agent, or Firm* — Barnes & Thornburg LLP

(57) ABSTRACT

A solid-phase permethylation procedure is described. For example, solid-phase permethylation can be utilized to prepare permethylated linear and branched, neutral and sialylated oligosaccharides, which can be analyzed by MALDI-MS.

12 Claims, 14 Drawing Sheets

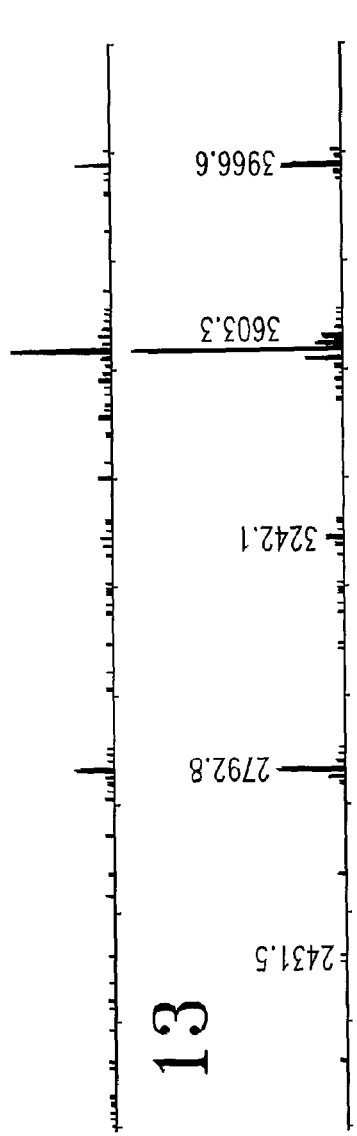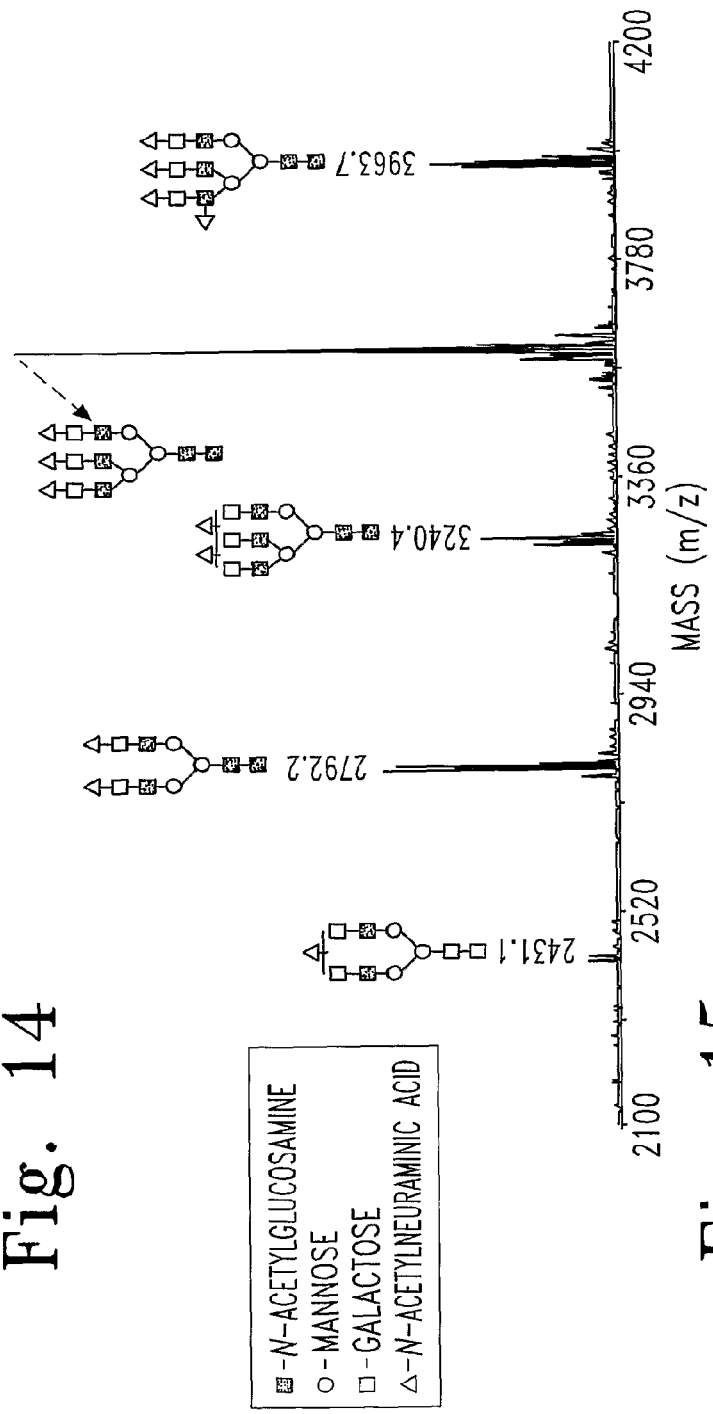
Fig. 13
Fig. 14
Fig. 15

PERMETHYLATION OF OLIGOSACCHARIDES

CROSS REFERENCE TO RELATED APPLICATION

This application is a divisional application of U.S. application Ser. No. 11/817,436, filed Aug. 30, 2007, which is a U.S. national counterpart application under 37 C.F.R. §371(b) of PCT international application serial no. PCT/US2006/007854 filed Mar. 3, 2006, which claims the benefit under 35 U.S.C. §119(e) of U.S. Provisional Application Ser. No. 60/658,295, filed Mar. 3, 2005, the disclosure of which is hereby incorporated herein by reference.

GOVERNMENT RIGHTS

This invention was made with government support under R01 GM24349 awarded by from the National Institutes of Health. The government has certain rights in the invention.

TECHNICAL FIELD OF THE DISCLOSURE

The present disclosure pertains to methods and apparatus for permethylation of oligosaccharides. In particular, the present disclosure pertains to solid-phase methods for permethylating oligosaccharides.

BACKGROUND

Structural aspects of oligosaccharides have been studied by mass spectrometry (MS) for many years. The development of matrix-assisted laser desorption/ionization mass spectrometry (MALDI-MS) and electrospray ionization mass spectrometry (ESI-MS) for oligosaccharides have accelerated substantially the acceptance and utilization of MS-based technologies during the last decade. In the structural analysis of complex oligosaccharides originating from various isolated glycoproteins, MALDI-MS in conjunction with exoglycosidase digestion and a tandem MS/MS operation have become particularly popular.

MALDI-MS structural analysis of oligosaccharides can, in general, be conducted with native, i.e., underivatized, oligosaccharides. There are, however, several reasons for conversion of oligosaccharides into their permethylated derivatives. These reasons include a facile determination of i) branching, ii) interglycosidic linkages, and iii) the presence of configurational and conformational isomers. Permethylation also stabilizes sialic acid residues in acidic oligosaccharides, thereby yielding more predictable ion products when such oligosaccharides are subjected to MS/MS experiments, and permitting simultaneous analysis of neutral and sialylated oligosaccharides. Further, methylated sugars resulting from permethylation ionize more efficiently than their native, i.e., underivatized, counterparts. Permethylated oligosaccharides, being compatible with reversed-phase liquid chromatography (RPLC), also permit RPLC separation of permethylated oligosaccharides in complex oligosaccharide mixtures prior to MS analysis.

Current permethylation procedures, employed over a number of years in oligosaccharide analysis, are based on solution-phase methodologies. The currently more widespread solution-phase approach for permethylation is based on the addition of methyl iodide to oligosaccharides, which are dissolved in dimethyl sulfoxide (DMSO) containing powdered sodium hydroxide (NaOH). Although this solution-phase method is effective for replacing protons at oxygen and nitrogen sites in oligosaccharides, and has been used successfully in various MS structural studies of complex oligosaccharides, it is a multi-step procedure involving excessive, time-consuming sample handling steps and requiring excessive sample clean-up. Further, current solution-phase methods appear less satisfactory when low picomole to femtomole quantities of glycoprotein samples are available for permethylation, as is often the case when modern glycoanalysis of biological fluids and tissues is undertaken. This limitation is primarily due to oxidative degradation and "peeling," i.e., side reactions, associated with the high pH resulting from dissolving NaOH powder prior to liquid-liquid extractions in solution-phase permethylation methods. These side reactions are adversely prominent with low picomole to femtomole quantities of glycoprotein samples.

Accordingly, permethylation procedures are needed that provide rapidity, experimental simplicity, clean reaction products (i.e., a low incidence of side reactions), scalability, and effective replacement of protons with methyl groups at oxygen and nitrogen sites in oligosaccharides.

SUMMARY

Research directed to develop an on-line permethylation procedure for neutral and acidic oligosaccharides has revealed that solid-phase permethylation provides rapidity, experimental simplicity, and small-scale permethylation capability, while also affording quantitative permethylation of oligosaccharide samples. Solid-phase permethylation was also found to be amenable to miniaturization in microreactors, yielding picomole amounts of permethylated linear and branched, neutral and sialylated oligosaccharides that were easily analyzed by MALDI-MS. Further, while decreasing oxidative degradation and peeling side reactions and the need for excessive sample clean-up, solid-phase permethylation was successfully interfaced on-line with RPLC and MS during separation and analysis of complex oligosaccharide mixtures.

In one illustrative embodiment, a reactor, such as a microreactor, is described. In one aspect, the microreactor includes a container. In another aspect, the microreactor includes a base disposed within the container. In yet another aspect, the microreactor includes a solvent disposed within the container. In one illustrative variation, the microreactor includes a column, such as spin column, packed with a solid inorganic base, such as mesh beads of an inorganic base, in a polar, aprotic solvent. In another illustrative variation, the microreactor includes a fused-silica capillary packed with a solid inorganic base, such as a powdered inorganic base, in a polar, aprotic solvent.

In another illustrative embodiment, a reactor, such as a microreactor, for conducting solid-phase permethylation of oligosaccharides is described. In one aspect, the microreactor includes a container. In another aspect, the microreactor includes a base disposed within the container. In yet another aspect, the microreactor includes a polar, aprotic solvent disposed with the container, where the solvent includes an oligosaccharide and a source of methyl groups. In one illustrative variation, the microreactor includes a column, such as a spin column, packed with a solid inorganic base, such as mesh beads of an inorganic base, in a polar, aprotic solvent, where the solvent includes an oligosaccharide and a source of methyl groups. In another illustrative variation, the microreactor includes a fused-silica capillary packed with a solid inorganic base, such as a powdered inorganic base, in a polar, aprotic solvent, where the solvent includes an oligosaccharide and a source of methyl groups.

In another illustrative embodiment, a method for conducting solid-phase permethylation of oligosaccharides is described. In one aspect, the method includes infusing a polar, aprotic solvent through a reactor, such as a microreactor, which microreactor includes a container, and a base and a polar, aprotic solvent disposed within the container, where the solvent includes an oligosaccharide and a source of methyl groups. In another aspect, the method includes contacting the oligosaccharide with the source of methyl groups. In yet another aspect, the method includes collecting a permethylated oligosaccharide from the microreactor. In one illustrative variation, the method includes contacting an oligosaccharide with a source of methyl groups in a polar, aprotic solvent in a column, such as a spin column, packed with inorganic base mesh beads, while infusing the solvent through the spin column by centrifugation, which solvent is disposed within the spin column during permethylation. In another illustrative variation, the method includes contacting an oligosaccharide with a source of methyl groups in a polar, aprotic solvent in a fused-silica capillary packed with a powdered inorganic base, while infusing the solvent through the capillary by a means including a syringe, which solvent is delivered to the fused-silica capillary during permethylation.

In another illustrative embodiment, a method for analyzing oligosaccharides is described that includes conducting solid-phase permethylation of oligosaccharides to afford permethylated oligosaccharides, and analyzing the permethylated oligosaccharides by MS. In one illustrative variation, permethylated oligosaccharides are separated by RPLC prior to being analyzed by MS.

In another illustrative embodiment, an apparatus for interfacing permethylation of oligosaccharides on-line with separation and analysis of permethylated oligosaccharides is described. In one aspect, the apparatus includes a reactor, such as a microreactor, for conducting solid-phase permethylation of oligosaccharides. In another aspect, the apparatus includes a RPLC column. In another aspect, the apparatus includes a mass spectrometer, where the microreactor, RPLC column, and mass spectrometer are interconnected.

Additional features of the present invention will become apparent to those skilled in the art upon consideration of the following detailed description of illustrative embodiments exemplifying the best mode of carrying out the invention as presently perceived.

BRIEF DESCRIPTION OF THE DRAWINGS

FIG. 13 shows the MALDI-TOFMS profile of N-linked oligosaccharides derived from 0.5 μg of fetuin and permethylated using the solution-phase permethylation method.

FIG. 14 shows the MALDI-TOFMS profile of N-linked oligosaccharides derived from 0.5 μg of fetuin and permethylated using the spin-column solid-phase permethylation method.

FIG. 15 shows the MALDI-TOFMS profile of N-linked oligosaccharides derived from 0.5 μg of fetuin and permethylated using the fused-silica capillary solid-phase permethylation method.

DETAILED DESCRIPTION

Figure 5:
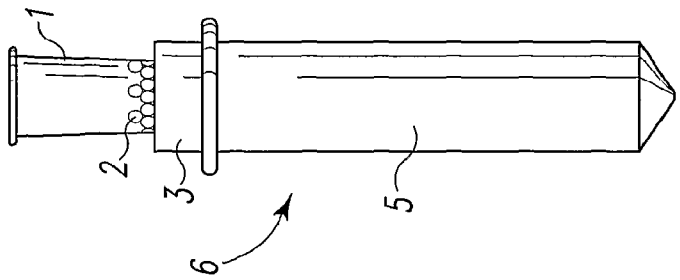
FIG. 5 shows a schematic representation of a centrifuge-ready spin column.
Figure 4:
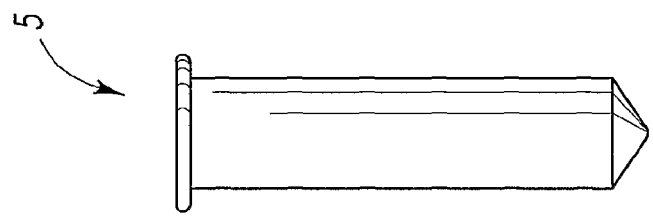
FIG. 4 shows a centrifuge tube.
Figure 3:
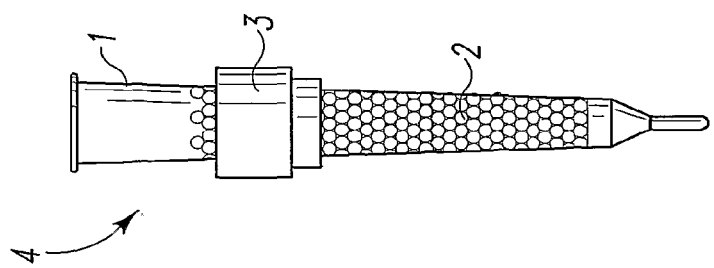
FIG. 3 shows a schematic representation of a spin column, packed with NaOH beads, fitted with a spin-column holder.
Figure 2:
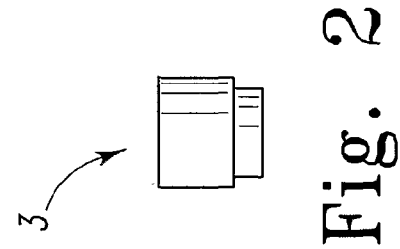
FIG. 2 shows a spin-column holder.
Figure 6:
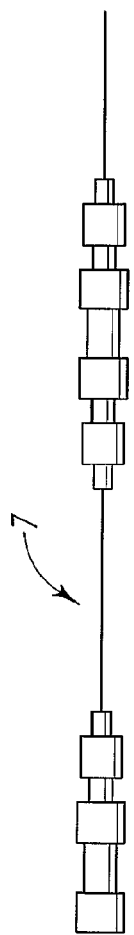
FIG. 6 shows a fused-silica capillary packed with a powdered inorganic base in a polar, aprotic solvent
Figure 7:
FIG. 7 shows a micro-syringe.
Figure 8:
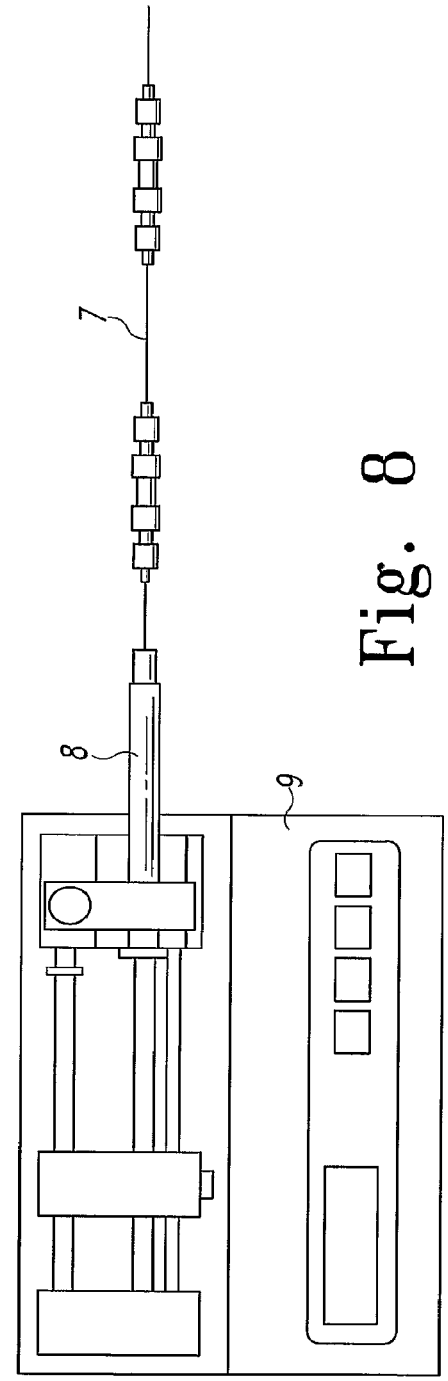
FIG. 8 shows a schematic representation of a fused-silica capillary, packed with a powdered inorganic base in a polar, aprotic solvent, connected to a micro-syringe and a syringe pump.

In one illustrative embodiment, a microreactor is described. However, it should be appreciated that a reactor other than a microreactor can be utilized. In one aspect, the microreactor includes a container. In another aspect, the microreactor includes a base disposed within the container. In yet another aspect, the microreactor includes a solvent disposed within the container. In one illustrative variation, and referring to FIG. 1, the microreactor includes a spin column 1 packed with inorganic base mesh beads 2 in a polar, aprotic solvent. As shown in FIG. 2 and FIG. 3, spin-column holder 3 is fitted to spin column 1 to prepare fitted spin column 4. Centrifuge tube 5 is shown in FIG. 4. Fitted spin column 4 is placed in centrifuge tube 5 to prepare centrifuge-ready spin-column 6, as shown in FIG. 5. In another illustrative variation, and referring to FIG. 6, the microreactor includes a fused-silica capillary 7 packed with a powdered inorganic base in a polar, aprotic solvent. As shown in FIG. 7 and FIG. 8, micro-syringe 8 and syringe pump 9 can be used in connection with fused-silica capillary 7. Illustratively, in either variation the inorganic base may be a metal hydroxide, such as NaOH, and other metal hydroxides such as LiOH, KOH, Mg(OH)$_2$, Ca(OH)$_2$, and the like, are contemplated to be within the scope of the invention; all such metal hydroxides being used as mesh beads in a spin column or in powdered form in a fused-silica capillary. Further, and again illustratively, in either variation the polar, aprotic solvent may be a solvent such as dimethylsulfoxide (DMSO), and other polar, aprotic solvents such as sulfolane, acetonitrile (ACN), hexamethylphosphoramide (HMPA), dimethylformamide (DMF), dimethylacetamide (DMA), N-methylpyrrolidone (NMP), and the like are contemplated to be within the scope of the invention.

In another illustrative embodiment, a microreactor for conducting solid-phase permethylation of oligosaccharides is described. However, it should be appreciated that a reactor other than a microreactor can be utilized. In one aspect, the microreactor includes a container. In another aspect, the microreactor includes a base disposed within the container. In yet another aspect, the microreactor includes a polar, aprotic solvent disposed with the container, where the solvent includes an oligosaccharide and a source of methyl groups. In one illustrative variation, and referring to FIG. 1, the microreactor includes a spin column 1 packed with inorganic base mesh beads 2 in a polar, aprotic solvent, where the solvent includes an oligosaccharide and a source of methyl groups. As shown in FIG. 2 and FIG. 3, spin-column holder 3 is fitted to spin column 1 to prepare fitted spin column 4. Centrifuge tube 5 is shown in FIG. 4. Fitted spin column 4 is placed in centrifuge tube 5 to prepare centrifuge-ready spin-column 6, as shown in FIG. 5. In another illustrative variation, and referring to FIG. 6, the microreactor includes a fused-silica capillary 7 packed with a powdered inorganic base in a polar, aprotic solvent, where the solvent includes an oligosaccharide and a source of methyl groups. As shown in FIG. 7 and FIG. 8, micro-syringe 8 and syringe pump 9 can be used in connection with fused-silica capillary 7. Illustratively, in either variation the inorganic base may be a metal hydroxide, such as NaOH, and other metal hydroxides such as LiOH, KOH, Mg(OH)$_2$, Ca(OH)$_2$, and the like are contemplated to be within the scope of the invention; all such metal hydroxides being used as mesh beads in a spin column or in powdered form in a fused-silica capillary. Further, and again illustratively, in either variation the polar, aprotic solvent may be a solvent such as dimethylsulfoxide (DMSO), and other polar, aprotic solvents such as sulfolane, acetonitrile (ACN), hexamethylphosphoramide (HMPA), dimethylformamide (DMF), dimethylacetamide (DMA), N-methylpyrrolidone (NMP), and the like are contemplated to be within the scope of the invention. Again illustratively, in either variation the source of methyl groups may be a methylating agent such as methyl iodide, and other methylating agents, such as methyl bromide, methyl triflate, and the like, are contemplated to be within the scope of the invention. Yet again illustratively, in either variation the oligosaccharide may be an N-linked oligosaccharide or an O-linked oligosaccharide.

In another illustrative embodiment, a method for conducting solid-phase permethylation of oligosaccharides is described. In one aspect, the method includes infusing a polar, aprotic solvent through a reactor, such as a microreactor, which microreactor includes a container, and a base and a polar, aprotic solvent disposed within the container, where the solvent includes an oligosaccharide and a source of methyl groups. In another aspect, the method includes contacting the oligosaccharide with the source of methyl groups. In yet another aspect, the method includes collecting a permethylated oligosaccharide from the microreactor. In one illustrative variation, the method includes contacting an oligosaccharide with a source of methyl groups in a polar, aprotic solvent in a spin column 1 packed with inorganic base mesh beads 2 (FIG. 1), while infusing the solvent through centrifuge-ready spin column 6 (FIG. 5) by centrifugation, which solvent is disposed within the spin column 1 during permethylation. In another illustrative variation, the method includes contacting an oligosaccharide with a source of methyl groups in a polar, aprotic solvent in a fused-silica capillary 7 packed with a powdered inorganic base, as shown in FIG. 6, while infusing the solvent through the capillary by means of syringe 8 (FIG. 7) and syringe pump 9 (FIG. 8), which solvent is delivered to the fused-silica capillary during permethylation. Illustratively, in either variation the inorganic base may be a metal hydroxide, such as NaOH, and other metal hydroxides such as LiOH, KOH, Mg(OH)$_2$, Ca(OH)$_2$, and the like are contemplated to be within the scope of the invention; all such metal hydroxides being used as mesh beads in a spin column or in powdered form in a fused-silica capillary. Further, and again illustratively, in either variation the polar, aprotic solvent may be a solvent such as dimethylsulfoxide (DMSO), and other polar, aprotic solvents such as sulfolane, acetonitrile (ACN), hexamethylphosphoramide (HMPA), dimethylformamide (DMF), dimethylacetamide (DMA), N-methylpyrrolidone (NMP), and the like are contemplated to be within the scope of the invention. Again illustratively, in either variation the source of methyl groups may be a methylating agent such as methyl iodide, and other methylating agents, such as methyl bromide, methyl triflate, and the like, are contemplated to be within the scope of the invention. Yet again illustratively, in either variation the oligosaccharide may be an N-linked oligosaccharide or an O-linked oligosaccharide.

In another illustrative embodiment, a method for analyzing oligosaccharides is described that includes conducting solid-phase permethylation of oligosaccharides to afford permethylated oligosaccharides, and analyzing the permethylated oligosaccharides by mass spectrometry. In comparing different solid-phase permethylation methods, i.e., spin-column solid-phase permethylation vs. fused-silica capillary solid-phase permethylation, four aspects deemed likely to affect permethylation efficiency (as measured by relative MS intensity of permethylated oligosaccharide) were evaluated, namely, sensitivity to i) sample flow rate (i.e., residence time) through the microreactor; ii) length of the microreactor; iii) amount of methyl iodide, and iv) frequency-of-use status of the microreactor. Spin-column 1 (FIG. 1) solid-phase permethylation involves a very simple procedure, in which the permethylation reaction can be completed through repeated passes of an oligosaccharide-containing sample over the packed mesh beads 2 (FIG. 1) of an inorganic base, for example, NaOH. Therefore, optimization experiments were focused on the fused-silica capillary microreactor 7 (FIG. 6-8), and the solid-phase permethylation method associated therewith. Conditions, which included the use of NaOH as the inorganic base, and DMSO as the polar, aprotic solvent, generally regarded as optimal for solution-phase permethylation were used initially and optimized for the fused-silica capillary solid-phase method. A specific parameter was varied while the other parameters were kept constant, and no major changes were observed for the studied parameter upon changing the values of the other parameters.

Figure 9:
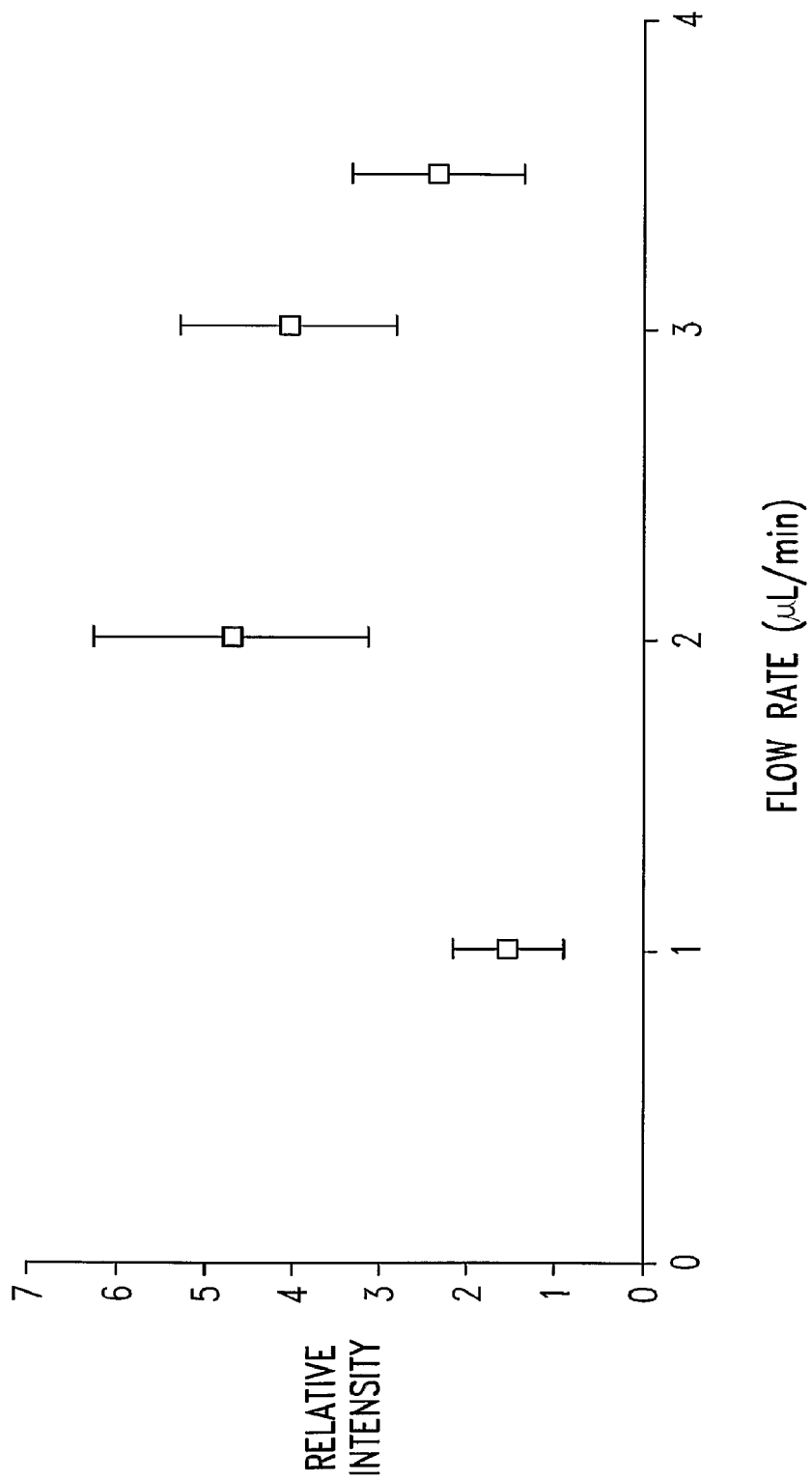
FIG. 9 shows the effect of flow rate on the efficiency of fused-silica capillary solid-phase permethylation of maltoheptaose.

One aspect of a method for analyzing oligosaccharides, which method includes conducting solid-phase permethylation of oligosaccharides and subsequent analysis of the resulting permethylated oligosaccharides by MS, is illustrated in FIG. 9 for a model permethylated oligosaccharide, i.e., maltoheptaose. FIG. 9 displays the sensitivity of such a method to sample flow rate through the microreactor 7, as measured by relative MS intensity of permethylated oligosaccharide, which flow rate is related to a residence time in the microreactor, or to reaction time. As an important criterion for solid-phase permethylation, the oligosaccharide sample and the reagent should have sufficient time to interact, i.e., to react, to complete the permethylation process. Advantageously, solid-phase permethylation does not depend on both diffusion and convection, whereas both diffusion and convection are necessary for solution-phase permethylation. Referring again to FIG. 9, it can be seen that the permethylation yield was lower at 1 µL/min flow, and also at higher flow rates, but it reached an optimum value at a sample flow rate of 2-3 µL/min. Apparently, a "fast" flow through the fused-silica capillary microreactor 7 does not allow for a sufficient interaction at the surface of packed NaOH, while very "low" flow rates may result in degradation of the oligosaccharide sample. A prolonged interaction of oligosaccharide with packed NaOH could promote peeling and oxidative degradation.

In solution-phase permethylation, where the optimum reaction time is known to be dependent on the NaOH/DMSO ratio, complete permethylation was achieved either at low or high NaOH/DMSO ratios, and long reaction times. In comparison to the fused-silica capillary solid-phase permethylation method, a low NaOH/DMSO ratio for solution-phase permethylation resembles "fast" flow rates in the fused-silica capillary solid-phase permethylation method, i.e., insufficient interaction time. Conversely, "high" NaOH/DMSO ratios for solution-phase permethylation are similar to a "slow" flow rate in the fused-silica capillary solid-phase permethylation method, where the amount of NaOH and reaction time remain unchanged. Thus, the flow rate in fused-silica capillary solid-phase permethylation appears to substitute for the NaOH/DMSO ratio in solution-phase permethylation, as the permethylation efficiency depends decidedly on flow rate. A flow rate of 3 µL/min (near optimum) was chosen in further optimization studies described below.

Figure 10:
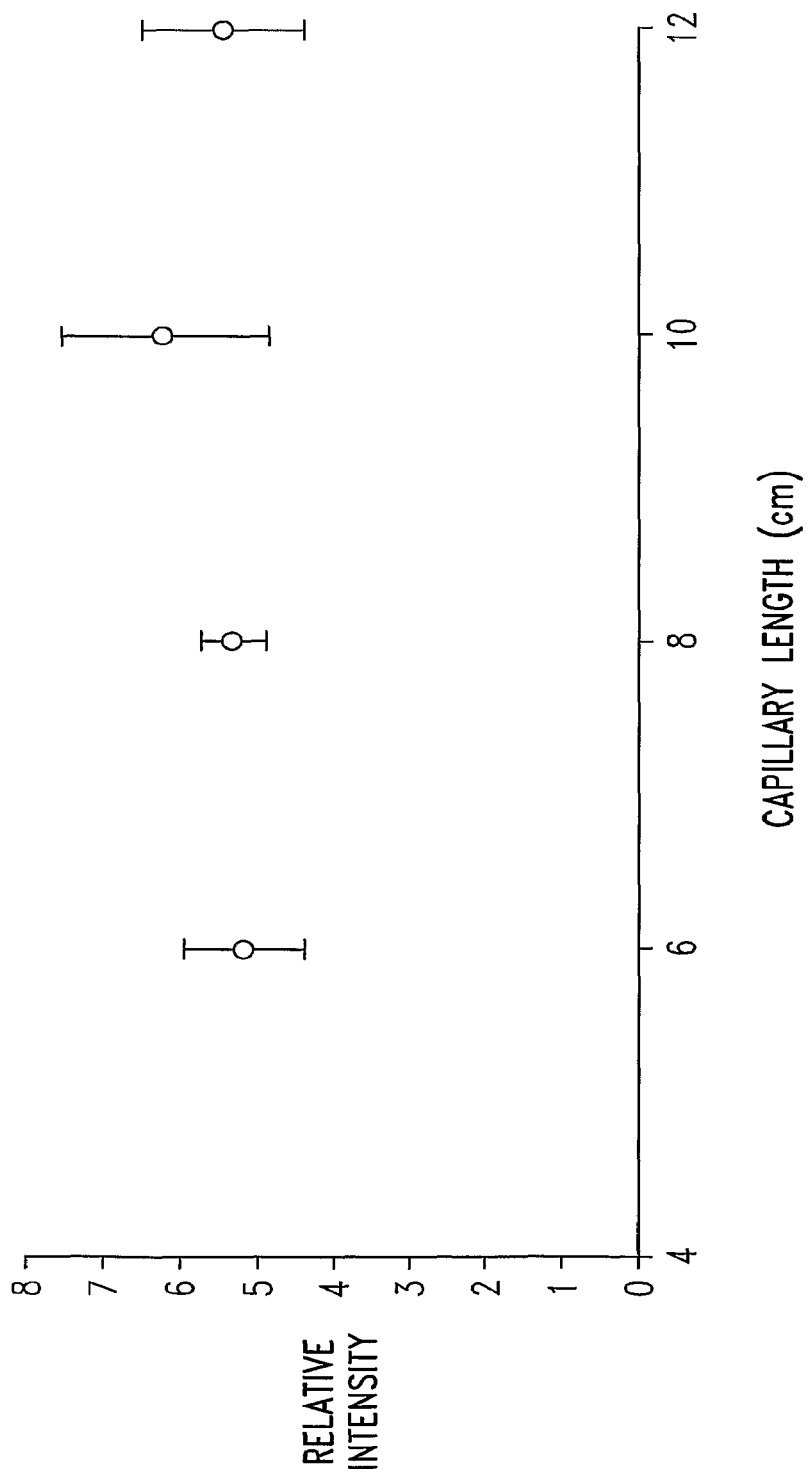
FIG. 10 shows the effect of capillary length on the efficiency of fused-silica capillary solid-phase permethylation of maltoheptaose at 3 μL/min flow rate.

A second aspect of a method for analyzing oligosaccharides, which method includes conducting solid-phase permethylation of oligosaccharides and subsequent analysis of the resulting permethylated oligosaccharides by MS, is illustrated in FIG. 10 for a model permethylated oligosaccharide, i.e., maltoheptaose. FIG. 10 displays the sensitivity of such a method to the length of the microreactor 7, as measured by relative MS intensity of permethylated oligosaccharide, which length is related to a residence time for the oligosaccharide in the microreactor 7. Referring again to FIG. 10, the relative intensities of MALDI-MS peaks for maltoheptaose were found to be relatively independent of the fused-silica capillary length at a constant flow rate of 3 µL/min. Apparently, permethylation reaction time was sufficient with a fused-silica capillary length of 6-10 cm. Further, although the oligosaccharide residence time in a 12-cm long fused-silica capillary is twice that in a 6-cm fused-silica capillary, the permethylation yield is similar. FIG. 10 also seems to indicate smaller standard deviations at a shorter fused-silica capillary length. Accordingly, 8-cm long fused-silica capillaries (near optimum, with lowest standard deviation) were utilized for the rest of this study.

Figure 11:
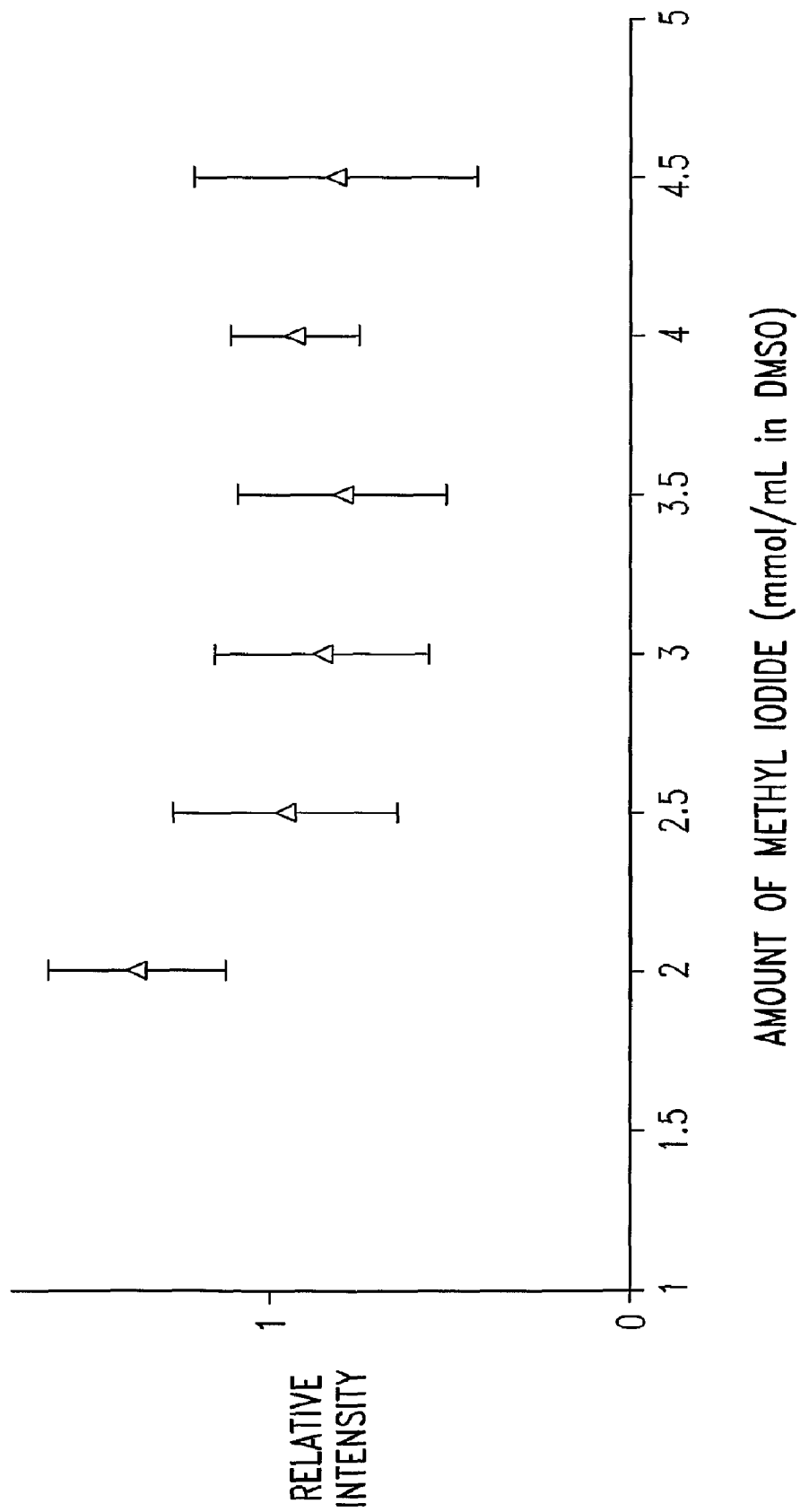
FIG. 11 shows the effect of methyl iodide amount on the efficiency of fused-silica capillary solid-phase permethylation of maltoheptaose at 3 μL/min flow rate.
Figure 12:
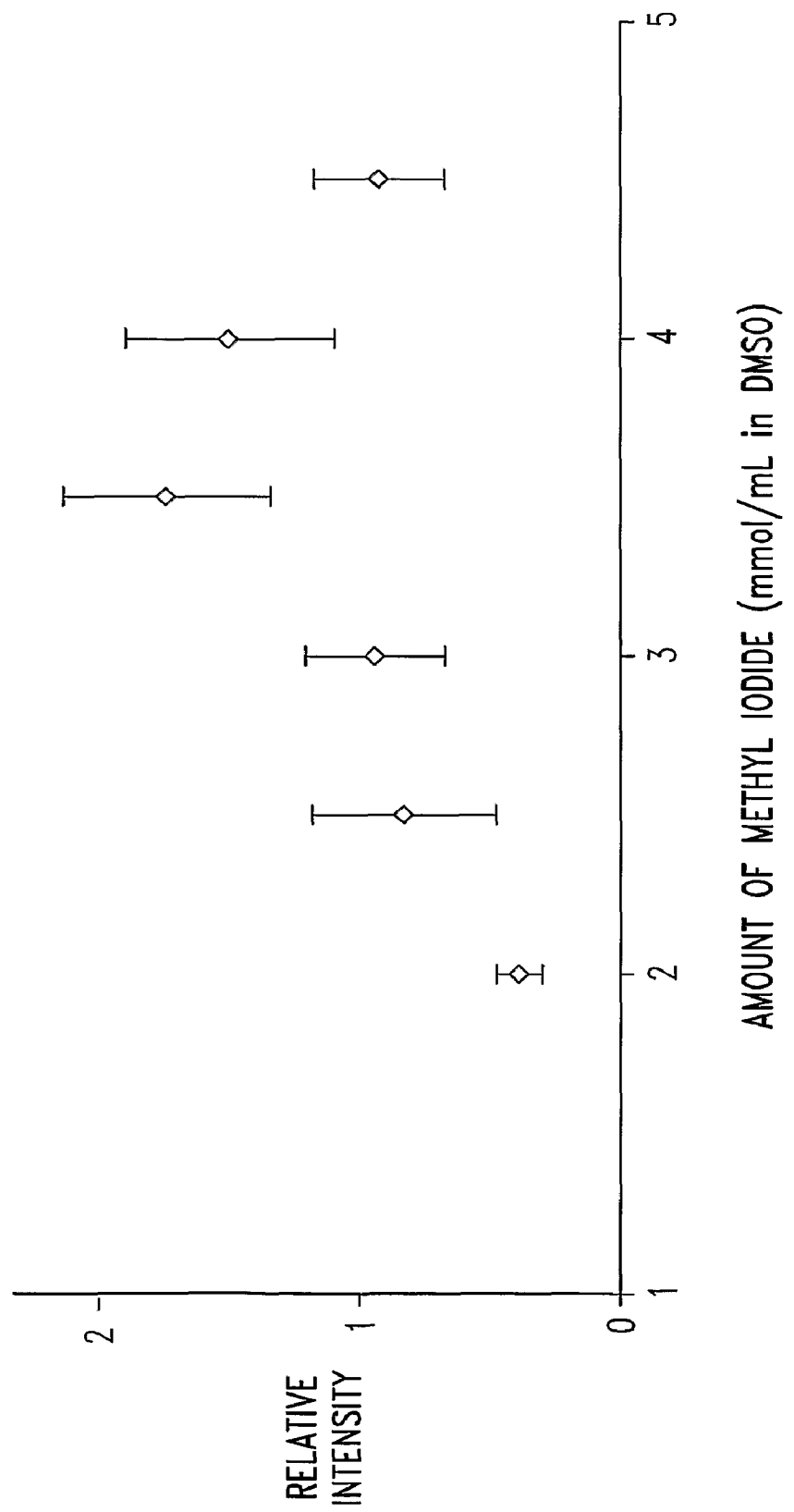
FIG. 12 shows the effect of methyl iodide amount on the efficiency of fused-silica capillary solid-phase permethylation of an N-linked oligosaccharide ((m/z 2792) derived from $\alpha_1$-acid glycoprotein) at 3 μL/min flow rate.

A third aspect of a method for analyzing oligosaccharides, which method includes conducting solid-phase permethylation of oligosaccharides and subsequent analysis of the resulting permethylated oligosaccharides by MS, is the sensitivity of such a method to the amount of methyl iodide, as measured by relative MS intensity of permethylated oligosaccharide. Evaluation of the effect of the amount of methyl iodide on permethylation efficiency was conducted both for maltoheptaose, a linear oligosaccharide, and a branched N-linked oligosaccharide derived from a glycoprotein. Referring to FIG. 11, the permethylation efficiency for maltoheptaose slightly decreased as the amount of methyl iodide increased. However, this decrease was within the error of measurement variation, indicating no substantial effect of the amount of methyl iodide for a linear oligosaccharide. As shown in FIG. 12, the situation was quite different for the more complex, branched N-linked oligosaccharide. Here, an optimum permethylation efficiency was attained at 3.5 mmol/mL of methyl iodide. Lower permethylation efficiencies were observed at lower and higher methyl iodide concentrations. This is in agreement with the results of solution-phase permethylation, since the optimum amount of methyl iodide for the solution-phase technique is a function of reaction time and the NaOH/DMSO ratio. Faster solution-phase permethylation is achieved using more methyl iodide. In the case of capillary permethylation, the reaction time is kept constant, so the amount of methyl iodide influences permethylation efficiency. Apparently, complex, branched N-linked oligosaccharides require more methyl iodide than linear oligosaccharides, owing presumably to steric hindrance due to branching in the former.

A fourth aspect of a method for analyzing oligosaccharides, which method includes conducting solid-phase permethylation of oligosaccharides and subsequent analysis of the resulting permethylated oligosaccharides by MS, is the sensitivity of such a method to the frequency-of-use status of the microreactor 7, which is related to the durability of the microreactor 7, i.e., its capacity for multiple and extended use. Solid-phase permethylation of maltoheptaose was performed at the end of every day over a seven-day period during which the microreactor 7 was utilized extensively to permethylate different samples. The microreactor 7 was continuously flushed with DMSO when not in use. No noticeable loss in permethylation efficiency, as measured by relative MS intensity of permethylated oligosaccharide, was observed after seven days of continuous use.

The efficiency of a solid-phase permethylation method in a fused-silica capillary microreactor 7 was compared directly to the efficiency of solid-phase permethylation method in a centrifuge-ready spin-column microreactor 6, and both were compared with the permethylation efficiency of a standard solution-phase method. N-linked oligosaccharides derived from fetuin, NaOH as the base, and DMSO as the solvent were used for this comparative study, which results were measured by relative MS intensity of permethylated oligosaccharide. Referring to FIG. 13-15, solid-phase permethylation in a fused-silica capillary microreactor 7, as shown in FIG. 15, provided the best permethylation results. Use of a spin-column microreactor 6, as shown by FIG. 14, was more efficient than the solution-phase permethylation method, as shown by FIG. 13, but not as efficient as the fused-silica capillary method. It should be appreciated that the fused-silica capillary solid-phase permethylation method decreases sample handling and sample degradation resulting from the use of extremely basic aqueous solution in the solution-phase method, which use may induce peeling reactions and/or oxidative degradation of oligosaccharides. This extreme condition appears completely avoidable when NaOH is packed in fused-silica capillaries or a spin column. The spin-column permethylation method showed high permethylation efficiency, while the reaction was complete in less than 1 min. However, the fused-silica capillary permethylation method appears to be similarly fast, if not faster, and highly effective for small amounts of sample. For every oligosaccharide tested, the fused-silica capillary solid-phase permethylation method was superior to the solution-phase method. While MS analysis of a solution-phase permethylated mixture of N-linked oligosaccharides derived from 0.1 µg of glycoprotein amounts was not feasible, the very same sample showed meaningful and reproducible MS results when fused-silica capillary solid-phase permethylation was utilized. A satellite peak preceding each peak in FIG. 13-15 is less than 5% intensity relative to the main peak and corresponds to under-permethylated oligosaccharides. The satellite peaks observed after the main peaks are due to adduct formation and impurities.

Figures 16, 17:
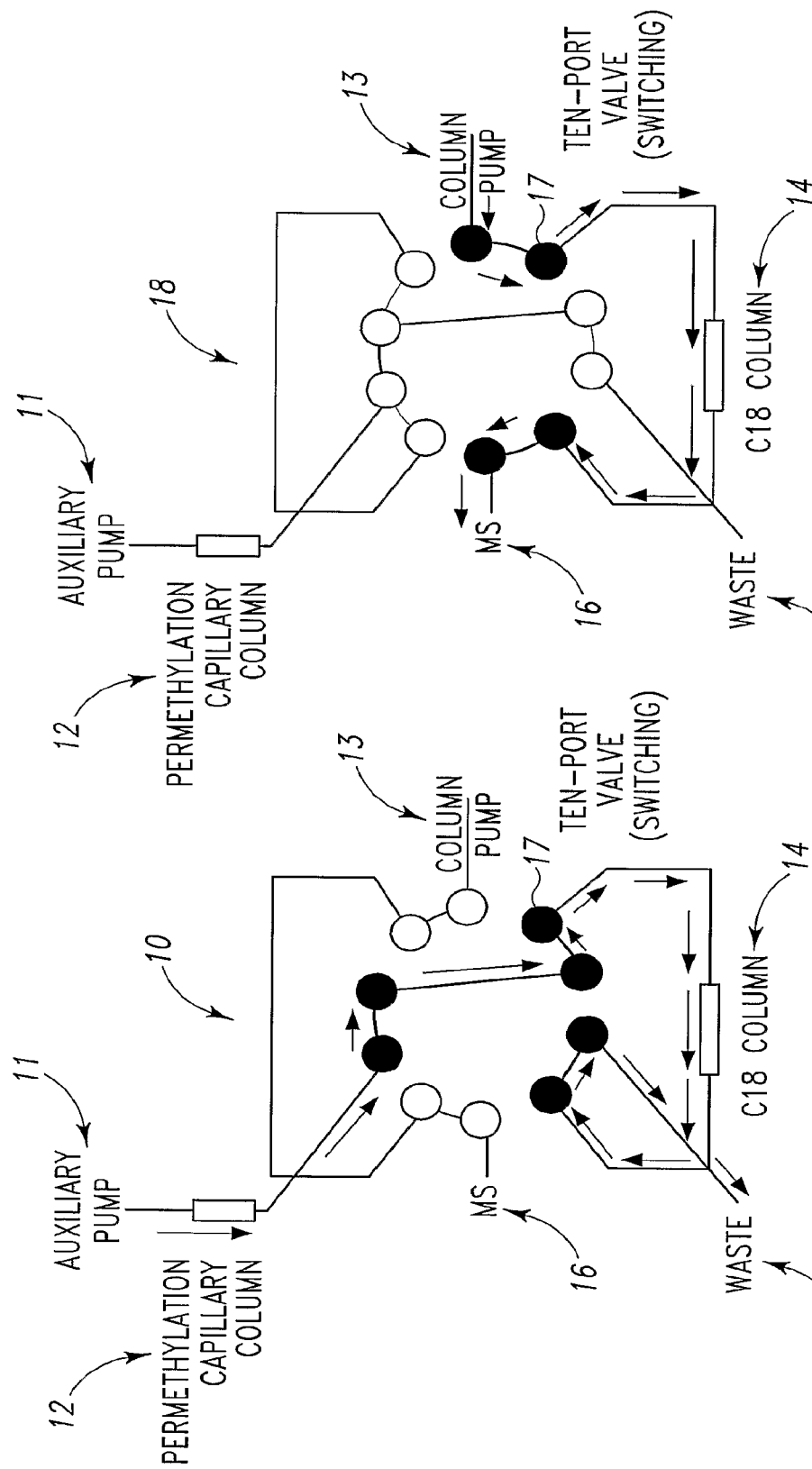
FIG. 16 shows a switching ten-port valve flow diagram for loading an on-line permethylated oligosaccharide sample onto a $C_{18}$ RPLC column.
FIG. 17 shows a switching ten-port valve flow diagram for $C_{18}$ RPLC separation and MS analysis of an on-line permethylated sample.

In another illustrative embodiment, an apparatus for interfacing solid-phase permethylation of oligosaccharides on-line with separation and analysis of permethylated oligosaccharides is described. In one aspect, and referring to FIG. 16, apparatus configuration 10 includes permethylation (fused-silica) capillary column 12, for conducting solid-phase permethylation of oligosaccharides, interconnected with $C_{18}$ column 14, for conducting desalting of permethylated oligosaccharides. Auxiliary pump 11 infuses oligosaccharides through permethylation (fused-silica) capillary column 12. Auxiliary pump 11 also pumps the resulting permethylated oligosaccharides through switching ten-port valve 17 onto $C_{18}$ column 14, where the permethylated oligosaccharides are trapped, washed and desalted with an equilibrating mobile phase, such as 20% methanol in water, and the resulting effluent then pumped to waste 15. In another aspect, and referring to FIG. 17, apparatus configuration 18 includes $C_{18}$ column 14, for conducting RPLC of desalted, permethylated oligosaccharides, interconnected with mass spectrometer MS 16, for conducting analysis of permethylated oligosaccharides by mass spectrometry. Column pump 13 pumps an eluting mobile phase gradient, such as 50% acetonitrile to 100% acetonitrile over a 20 min period, onto $C_{18}$ column 14 (then maintained for about 20 min) through switching ten-port valve 17, in order to elute desalted, permethylated oligosaccharides. The resulting effluent from $C_{18}$ column 14 is pumped by column pump 13 to mass spectrometer MS 16 for analysis by ESI-MS or MALDI-MS. When the former is used to analyze permethylated oligosaccharides, 0.1% formic acid is added to the mobile phase.

The following examples illustrate specific embodiments of the invention in further detail. These examples are provided for illustrative purposes only and should not be construed as limiting the invention or the inventive concept to any particular physical configuration in any way. Numerous modifications and changes to the basic invention may be made by those of ordinary skill in the art without departing from the spirit of the invention.

Materials for examples were obtained from the following sources: Maltoheptaose, pancreatic bovine ribonuclease B, fetuin from fetal calf serum, human $\alpha_1$-acid glycoprotein, bile salt-stimulated lipase (BSSL), proteomics-grade trypsin, PNGase F, tris-(hydroxymethyl)aminomethane hydrochloride (Tris-HCl), ethylenediaminetetraacetic acid (EDTA), and ethylene glycol-bis(β-aminoethyl ether)-N,N,N',N'-tetraacetic acid (EGTA) were obtained from Sigma (St. Louis, Mo., USA). The MALDI matrix, 2,5-dihydroxybenzoic acid (DHB), borane-ammonia complex, and NaOH were purchased from Aldrich (Milwaukee, Wis., USA). Chloroform, methyl iodide, and sodium chloride were obtained from EM Science (Gibbstown, N.J., USA). Dithiothreitol (DTT), iodoacetamide, and 3-([3-cholamidopropyl]dimethylammonio)-1-propanesulfonate (CHAPS) were purchased from Bio-Rad Laboratories (Hercules, Calif., USA). Ammonium bicarbonate was obtained from Mallinckrodt Chemical Company (Paris, Ky., USA), and sodium pyrophosphate was obtained from J. T. Baker, Inc. (Phillipsburg, N.J., USA). Acetonitrile (ACN) and hydrochloric acid solution N/10 were purchased from Fisher Scientific (Fair Lawn, N.J., USA). All permethylation conditions, including sample amount, amount of methyl iodide, and water/chloroform sample extraction, were maintained constant to ensure a valid quantitative comparison.

EXAMPLE 1

Solution-Phase Permethylation

Maltoheptaose and all N-linked oligosaccharides derived from glycoproteins were permethylated as follows: Briefly, methyl iodide, a trace of water, and NaOH powder were suspended in DMSO and mixed for 10 min at room temperature. Typically, 1-10 µg of sample were suspended in 30 µL of DMSO, to which 3.6 mg of NaOH powder, 0.3 µL of water, and 5.6 µL of methyl iodide were added.

EXAMPLE 2

Spin-Column Solid-Phase Permethylation

Figure 1:
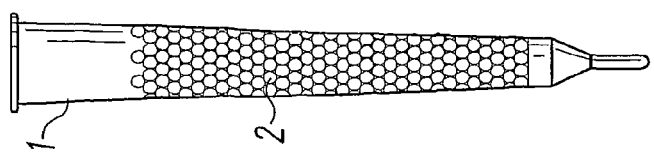
FIG. 1 shows a schematic representation of a spin column packed with mesh beads of an inorganic base in a polar, aprotic solvent.

Spin columns 1 obtained from Harvard Apparatus (Holliston, Mass., USA) were packed with NaOH mesh beads 2 (FIG. 1). NaOH beads were first suspended in ACN, thus preventing atmospheric moisture absorption. The ACN-suspended NaOH beads were then packed in a spin column to about 3-cm depth. Prior to sample application, a spin column 1 was fitted with a spin-column holder 3 (FIG. 2), and the resulting fitted spin column 4 (FIG. 3) was placed in a centrifuge tube 5 (FIG. 4) to prepare a spin-column solid-phase microreactor 6 (FIG. 5), and spun down at 1000 rpm for 2 min. The NaOH-packed spin column was then washed several times with DMSO.

The ratios of DMSO, methyl iodide, water, and sample were the same as in solution-phase permethylation. For both the spin-column and fused-silica capillary solid-phase permethylation, the amount of NaOH used was the same, aside from the experiments involving the optimization of the fused-silica capillary length. The sample, methyl iodide, and trace of water were mixed immediately before being applied to the spin-column solid-phase microreactor 6 (FIG. 5). Next, the sample was infused through microreactor 6, utilizing a low spin speed (1000 rpm) while it was collected. The removal of DMSO was accomplished by the use of chloroform as described for the solution-phase permethylation approach.

EXAMPLE 3

Fused-Silica Capillary Solid-Phase Permethylation

Fused-silica capillaries (500 µm i.d.) from Polymicro Technologies (Phoenix, Ariz., USA) were used. Tubes, nuts and ferrules from Upchurch Scientific (Oak Harbor, Wash., USA) were employed to assemble the capillary set. To protect the packing material from moisture, NaOH powder was suspended in ACN immediately after crushing the NaOH beads. The powdered NaOH in ACN was then packed inside 500 µm i.d. fused-silica capillaries by using pressure to prepare a fused-silica capillary solid-phase microreactor 7 (FIG. 6). A 100-μL Hamilton syringe 8 (FIG. 7) and a syringe pump 9 (FIG. 8) from KD Scientific, Inc. (Holliston, Mass., USA) were employed to introduce a sample solution into the fused-silica capillary solid-phase microreactor 7 (FIG. 8). The microreactor setup was assembled after packing the fused-silica capillary with NaOH and ACN. DMSO was infused into the packed capillaries with NaOH to replace ACN prior to analysis.

Fused-silica capillary solid-phase permethylation employed the same chemical ratios as those used in solution-phase permethylation. For both the spin-column and fused-silica capillary solid-phase permethylation, the amount of NaOH used was the same, aside from the experiments involving the optimization of the fused-silica capillary length. Samples were prepared in DMSO, containing methyl iodide and a trace of water. Next, the samples were infused through the packed, fused-silica capillary solid-phase microreactor 7 (FIG. 6) at an appropriate flow rate by means of micro-syringe 8 (FIG. 7) and syringe pump 9 (FIG. 8), while they were collected at the capillary end. The removal of DMSO was accomplished by the use of chloroform as described for the solution-phase permethylation approach.

EXAMPLE 4

Extraction of Permethylated Oligosaccharide Samples

Permethylated oligosaccharides and maltoheptaose were extracted with chloroform and washed repeatedly with water. For solution-phase permethylation, ice-cold water was added to the permethylation mixture and placed in an ice-bath prior to the addition of chloroform. The mixture was then vortexed for several minutes. The aqueous layer was then discarded and the chloroform layer washed repeatedly with water. The pH of the aqueous layer was continuously monitored with pH indicators, while 5-fold washing with water was deemed sufficient to eliminate residual NaOH, any side products and excess methyl iodide.

EXAMPLE 5

Extraction of Glycoproteins from Tissue and Release of their N-Linked Oligosaccharides or O-Linked Oligosaccharides N-Linked oligosaccharides were enzymatically released from ribonuclease B, fetuin, and $a_1$-acid glycoprotein using PNGase F. This enzymatic release was performed as follows: Briefly, individual glycoproteins or a mixture of the three model glycoproteins were suspended in 10 mM sodium phosphate buffer (pH 7.5) containing 0.1% mercaptoethanol. The sample was thermally denatured by incubation at 95° C. for 5 mM. Next, the sample was allowed to cool to room temperature prior to the addition of 5 mU of PNGase F. Finally, the reaction mixture was incubated for 3 h at 37° C. Peptides were eliminated from the mixture by passing the reaction mixture over a $C_{18}$ cartridge, while collecting the effluent. Finally, the collected effluent containing released N-linked oligosaccharides was dried under vacuum and subsequently permethylated.

Although there are many lysis buffers that are commercially available and commonly utilized in proteomics, none seemed suitable for a glycomic analysis following protein and glycoprotein extractions. Accordingly, a lysis buffer was developed that is efficient and suitable for the extraction of proteins and glycoproteins without interfering with the MALDI-MS analysis of released oligosaccharides. The total proteome sample was extracted by suspending a homogenized tissue in the lysis buffer composed of 20 mM Tris-HCl (pH 7.5), 150 mM sodium chloride, 1 mM disodium EDTA, 1 mM EGTA, 2.5 mM sodium pyrophosphate and 0.5% CHAPS. Next, the mixture was sonicated for 15 min and shaken for 1 h at 4° C. The extract was then centrifuged at 30,000 rpm for 1.5 h at 4° C. The supernatant layer containing a cytosolic part of the proteome was then reduced and alkylated prior to the addition of trypsin. Briefly, the extracted total proteome sample was suspended in 100 μL of 100 mM ammonium bicarbonate buffer solution, to which 40 μL of 10 mM DTT solution were added and incubated at 56° C. for 45 min. After cooling, 40 μL of 55 mM iodoacetamide prepared in 100 mM ammonium bicarbonate buffer solution were added to the mixture and it was incubated at room temperature for 30 mM in the dark. Next, trypsin was added to the reduced and alkylated mixture, continuing incubation at 37° C. for 18 h. The action of trypsin was quenched through heating the reaction mixture at 95° C. for 10 mM. Then, 5 mU of PNGase F were added to the reaction mixture (to release N-linked oligosaccharides) and it was incubated at 37° C. overnight. Peptides were eliminated from the mixture by passing the reaction mixture over a $C_{18}$ cartridge, while collecting the effluent. Finally, the collected effluent containing released N-linked oligosaccharides was dried under vacuum and subsequently permethylated.

O-Linked oligosaccharides were typically released from glycoprotein samples as follows: Glycoprotein samples were prepared as aqueous solution at 10 mg/mL concentrations. Small aliquots (1-5 μL) were transferred to a microtube and dried under nitrogen. Next, a 10-μL volume of borane-ammonia complex solution (prepared at 5 mg/mL in 28% aqueous ammonia solution) was added, while the mixture was subsequently incubated at 45° C. for 18-24 h. The reaction mixtures were then loaded onto a microcolumn made from a micropipette tip packed with a 20-uL volume of SP20SS resin (bottom) and 40 uL cation-exchange resin ($H^+$ form) (top) volume. A 200-μL volume of aqueous effluent was collected and lyophilized. Residual boric acid was removed through several additions of 200 μL of methanol and evaporation.

EXAMPLE 6

MALDI-MS and ESI-MS Spotting

The dried permethylated sample was resuspended in 50:50 methanol/water solution, containing 2.5 mM sodium acetate, to promote complete sodium adduct formation in MALDI-MS. The sample was then spotted directly on the MALDI plate and mixed with an equal volume of the DHB matrix, which was, in turn, prepared by suspending 10 mg of DHB in 1 mL of 50:50 water/methanol solution to produce a 10 mg/mL matrix solution. The sample spot was then dried under vacuum to ensure uniform crystallization. Native maltoheptaose was utilized as an internal standard in the case of the optimization studies. Samples for ESI-MS were prepared in similar fashion. The intensities of the permethylated oligosaccharides were reported as relative intensities to that of the internal standard.

EXAMPLE 7

Instrumentation

An Applied Biosystems 4700 proteomics analyzer (Applied Biosystems, Framingham, Mass., USA) was utilized for MALDI/TOF TOF/MS. This instrument was equipped with an Nd:YAG laser with a 355-nm wavelength. MALDI spectra were acquired in the positive-ion mode. MS data were further processed using DataExplorer 4.0 (Applied Biosystems). A ThermoElectron ESI/Ion-trap instrument MS (ThermoElectron Corporation, Waltham, Mass., USA) was used for ESI-MS. Fused-silica capillary solid-phase permethylation was conducted on-line using the apparatus depicted in FIG. 16 and FIG. 17, as described herein.

EXAMPLE 8

Applications of Solid-Phase Permethylation to Glycomic Analysis

Figure 18:
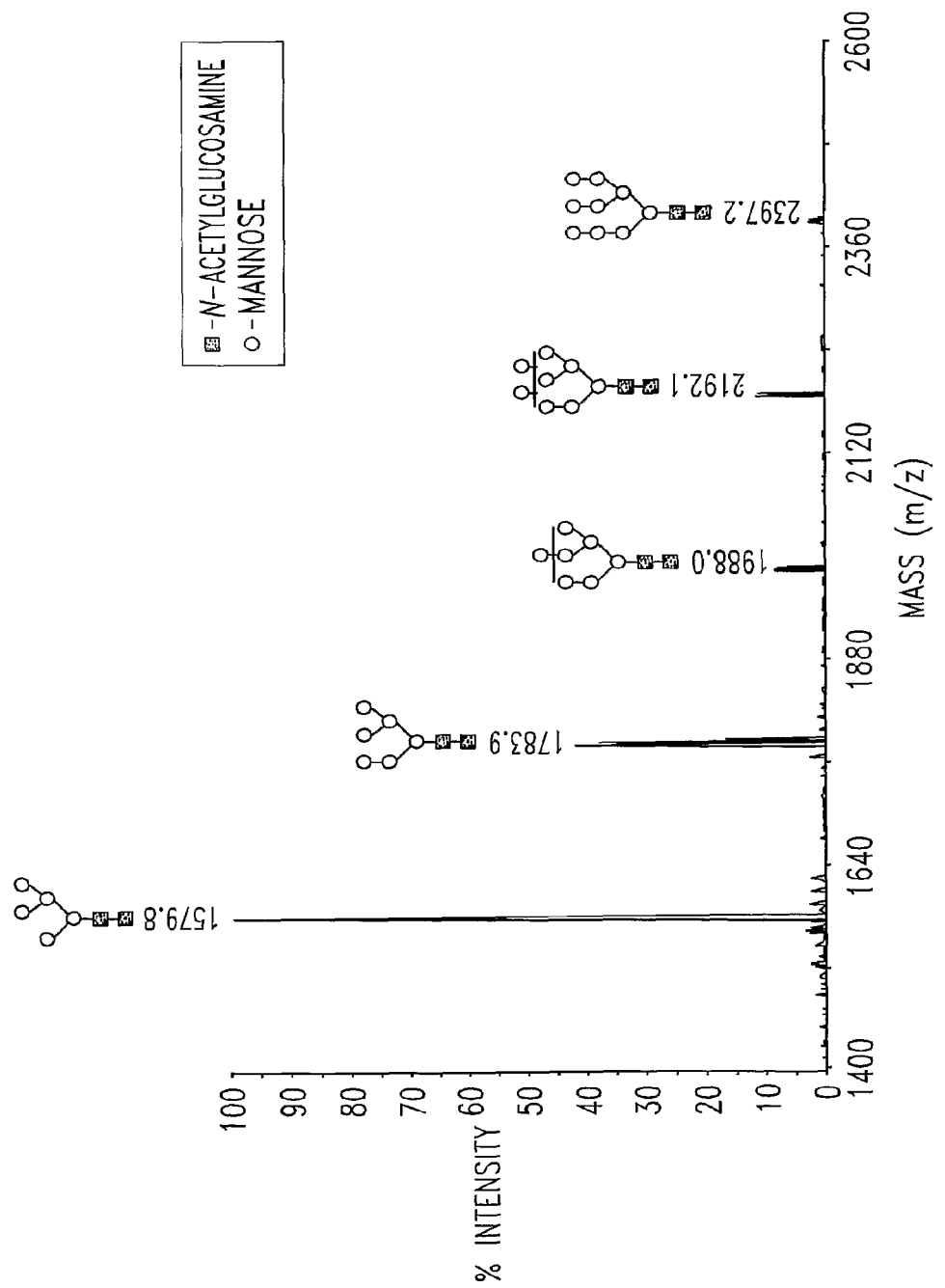
FIG. 18 shows the MALDI-TOFMS profile of N-linked oligosaccharides derived from 0.5 μg of ribonuclease B and permethylated using the fused-silica capillary solid-phase permethylation method.

After determining that various model oligosaccharides (neutral, branched, and sialylated structures) were rapidly and effectively permethylated at picomole levels using the fused-silica capillary solid-phase permethylation method, the applicability of fused-silica capillary solid-phase permethylation to the high-mannose N-linked oligosaccharides derived from ribonuclease B was determined. The glycoprofile of Man5 through Man9 structures is shown in FIG. 18. The relative peak intensities of all structures in this profile are reflective of the typical abundance seen in many laboratories, suggesting that efficient permethylation occurred with all oligosaccharides in this sample type.

Figure 19:
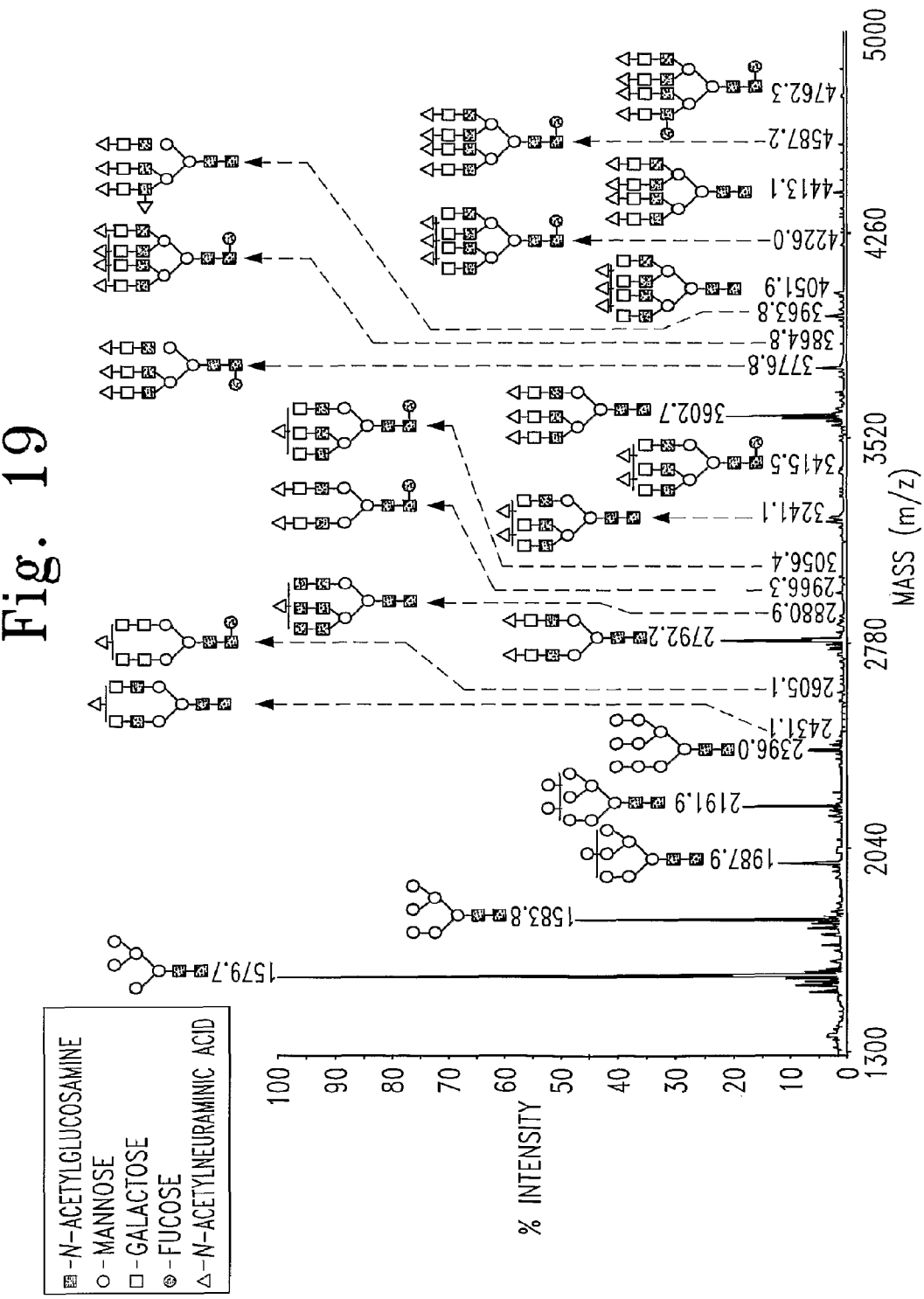
FIG. 19 shows the MALDI-TOFMS profile of N-linked oligosaccharides derived from a 0.5 μg mixture of ribonuclease B, fetuin, and $\alpha_1$-acid glycoprotein and permethylated using the fused-silica capillary solid-phase permethylation method.
Figure 20:
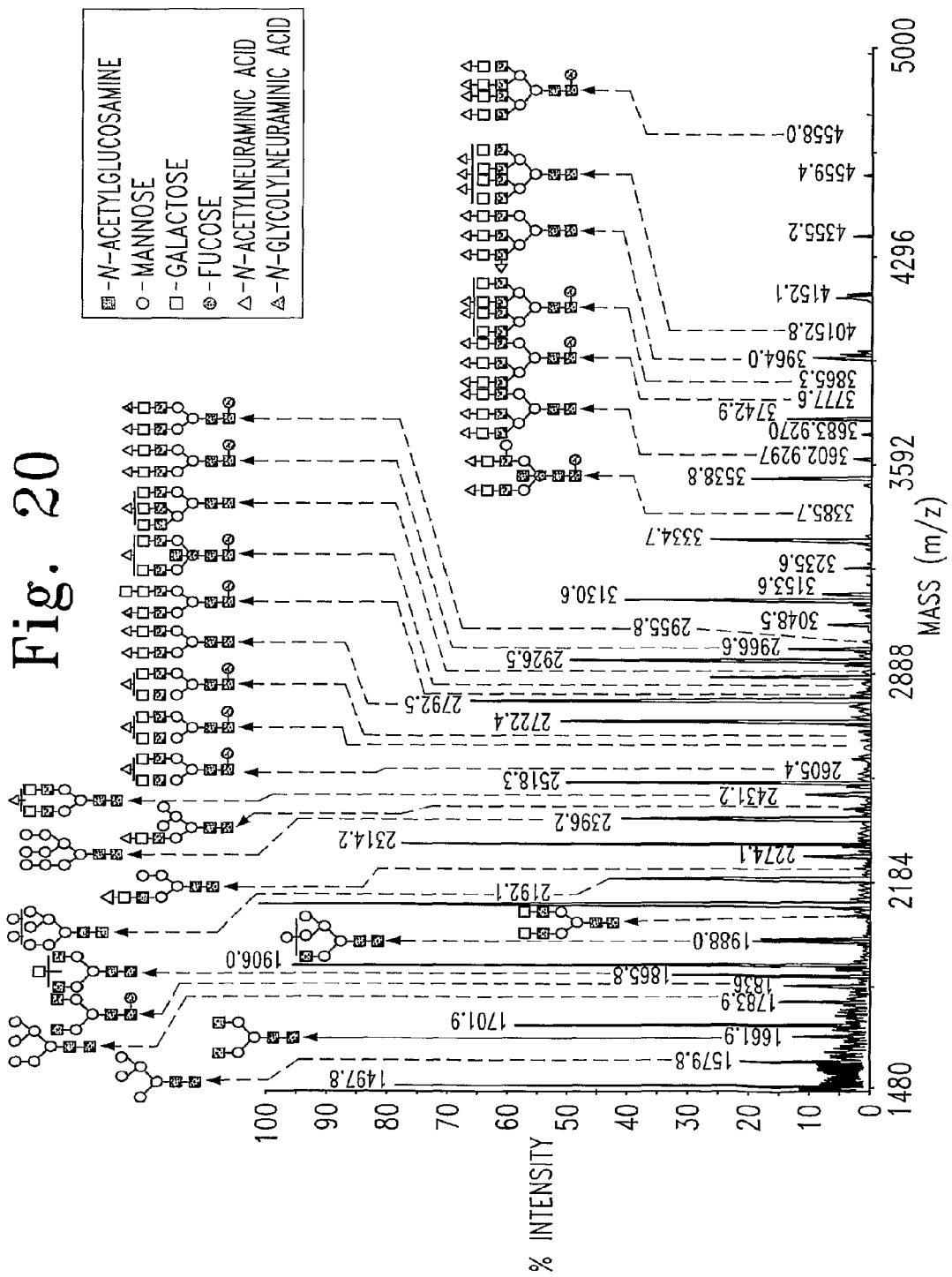
FIG. 20 shows the MALDI-TOFMS profile of N-linked oligosaccharides derived from 20 mg of rat liver tissue and permethylated using the fused-silica capillary solid-phase permethylation method.
Figure 21:
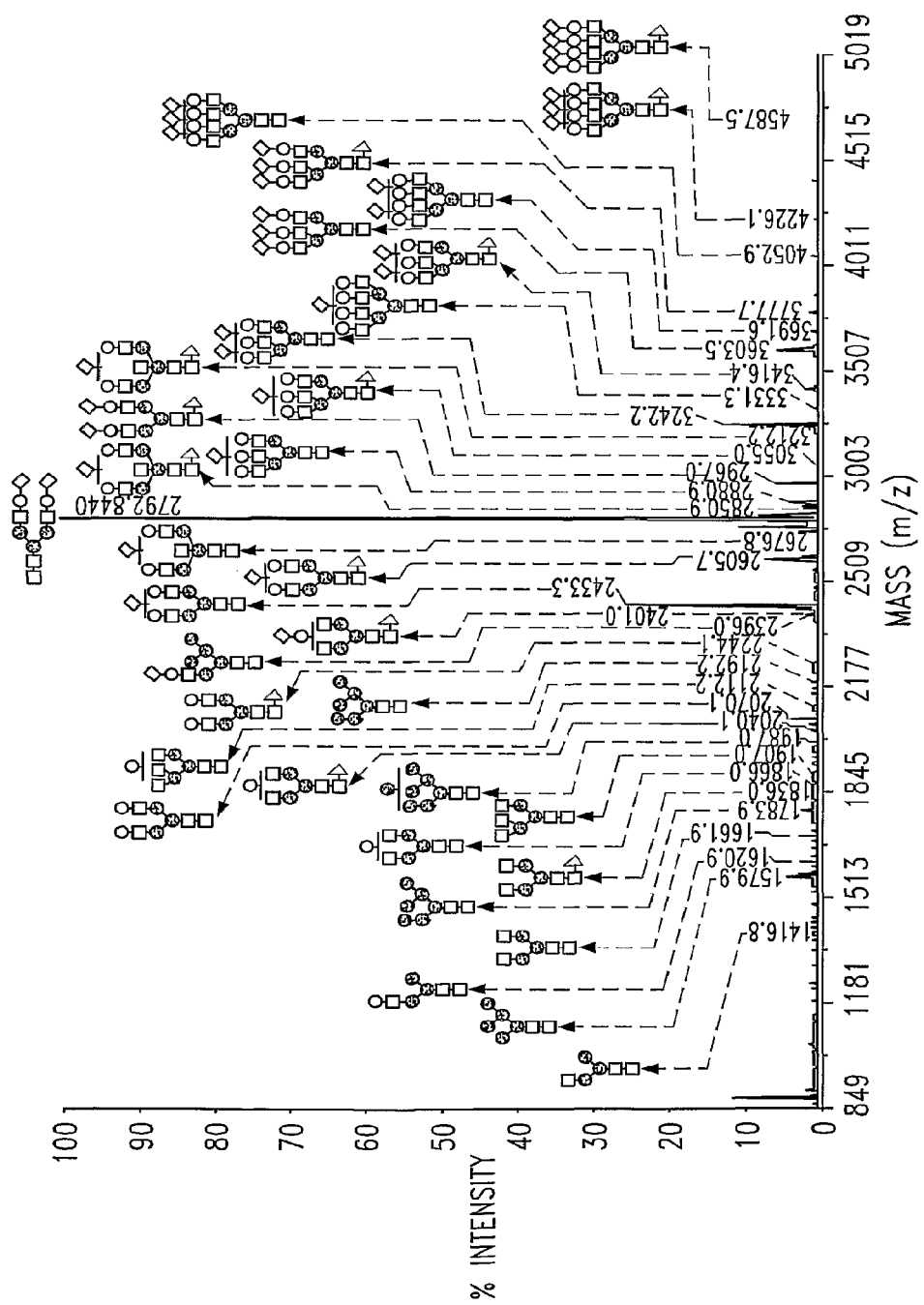
FIG. 21 shows the MALDI-TOFMS profile of N-linked oligosaccharides derived from human blood serum of a Stage II breast cancer patient and permethylated using the fused-silica capillary solid-phase permethylation method.

The fused-silica capillary solid-phase permethylation procedure was also utilized for the permethylation of sialylated oligosaccharides, as illustrated in FIG. 15 and FIG. 19 for the sialylated N-linked oligosaccharides derived from bovine fetuin and human $\alpha_1$-acid glycoprotein, respectively. Once again, the relative intensities of the permethylated sialylated oligosaccharides derived from both glycoproteins reflect their expected content. N-Linked oligosaccharides derived from a 0.5 µg mixture of ribonuclease B, fetuin, and $\alpha_1$-acid glycoprotein were also permethylated successfully, as illustrated in FIG. 19. The applicability of the fused-silica capillary solid-phase permethylation method to highly heterogeneous mixtures was further illustrated for the total glycome derived from rat liver tissue, as shown in FIG. 20, and the N-linked oligosaccharide profile from human blood serum of a Stage II breast cancer patient, as shown in FIG. 21.

Figure 22:
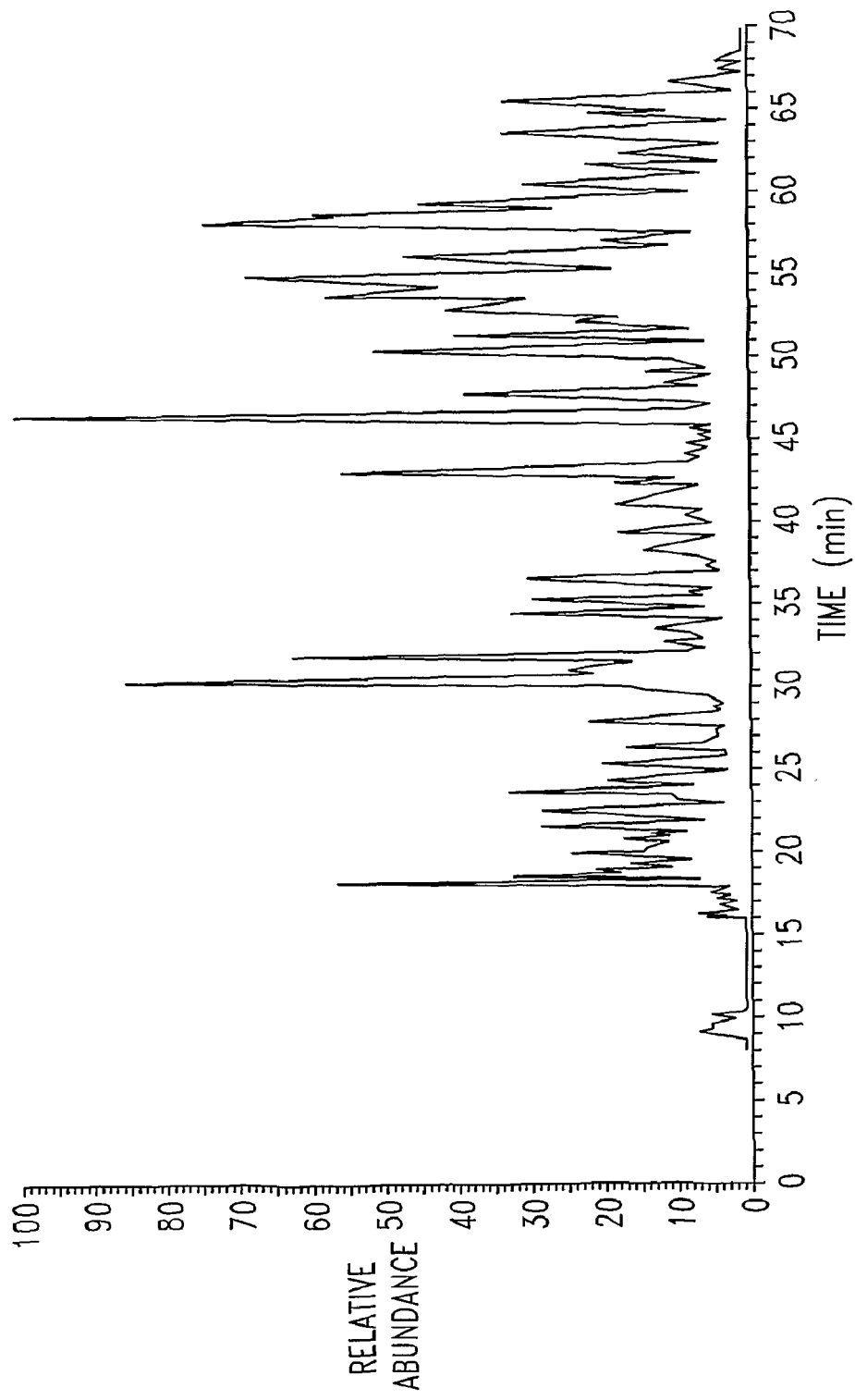
FIG. 22 shows the nano-LC/ESI-MS profile of reduced N-linked and O-linked oligosaccharides derived from BSSL and permethylated using the fused-silica capillary solid-phase permethylation method.
Figure 23:
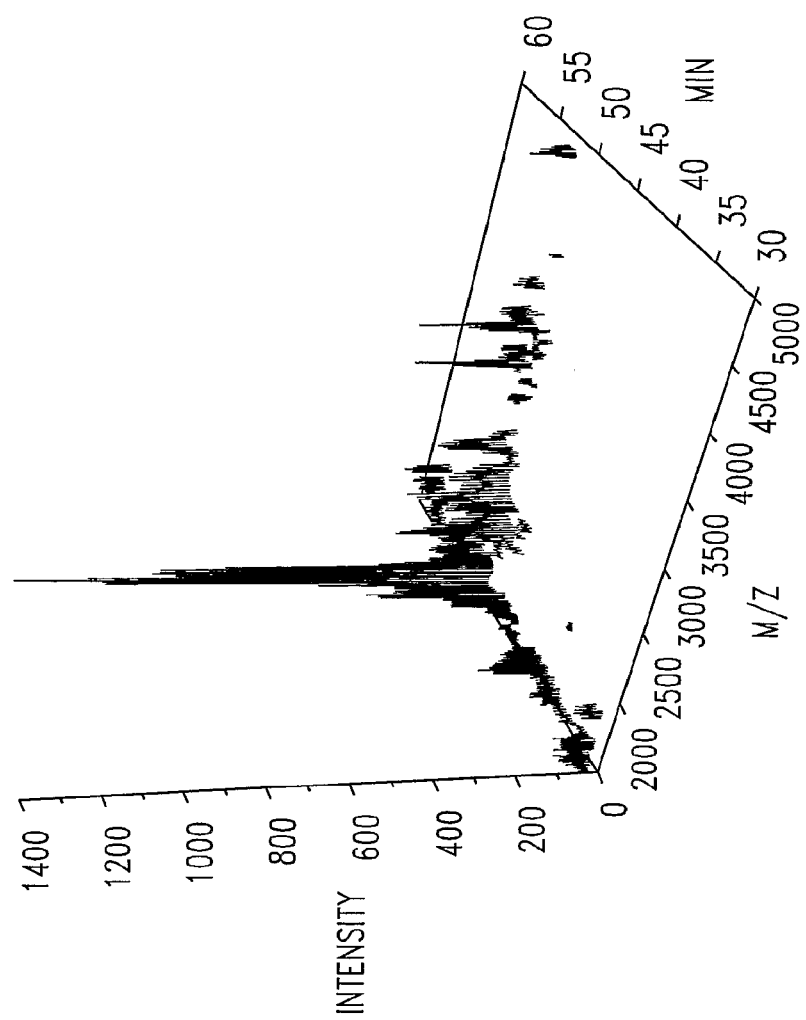
FIG. 23 shows the LC/MALDI/TOF/TOFMS profile of reduced N-linked and O-linked oligosaccharides derived from human blood serum and permethylated using the fused-silica capillary solid-phase permethylation method.

The fused-silica capillary solid-phase permethylation procedure was also utilized on-line in tandem with RPLC and MS for the permethylation, separation, and analysis, respectively, of reduced N-linked and O-linked oligosaccharides derived from BSSL, and reduced N-linked oligosaccharides derived from human blood serum, as illustrated in FIG. 22 and FIG. 23, respectively, thereby demonstrating the on-line interfacing of solid-phase permethylation with RPLC and MS.

The use of solid-phase permethylation, including an on-line embodiment thereof, has been demonstrated herein for a variety of oligosaccharides and heterogeneous mixtures of oligosaccharides derived from different glycoproteins. Moreover, solid-phase permethylation has been shown to be amenable to derivatizing trace amounts of oligosaccharides, as deduced from the ability to permethylate oligosaccharides derived from submicrogram amounts of glycoproteins.

The invention claimed is:

1. A method for conducting solid-phase permethylation of oligosaccharides in a reactor, the method comprising:
    a) infusing a polar, aprotic solvent through a packed inorganic base in the reactor, wherein the solvent includes an oligosaccharide and a source of methyl groups;
    b) contacting the oligosaccharide with the source of methyl groups; and
    c) collecting a permethylated oligosaccharide.

2. The method of claim 1, wherein the reactor comprises:
    a) a container;
    b) the base disposed within the container; and
    c) the solvent disposed within the container.

3. The method of claim 2, wherein the infusing solvent is diposed within the container during permethylation.

4. The method of claim 2, wherein the infusing solvent is delivered to the container during permethylation.

5. The method of claim 2, wherein the container is a fused-silica capillary.

6. The method of claim 2, wherein the base is NaOH.

7. The method of claim 2, wherein the solvent is DMSO.

8. The method of claim 2, wherein the source of methyl groups is methyl iodide.

9. The method of claim 2, wherein infusing is carried out by centrifugation.

10. The method of claim 2, wherein infusing is carried out by a means including a syringe.

11. The method of claim 1, wherein the reactor is a microreactor.

12. The method of claim 2, wherein the reactor is a microreactor.

* * * * *